United States Patent
Horine et al.

(10) Patent No.: US 6,957,566 B1
(45) Date of Patent: Oct. 25, 2005

(54) MEASURING IN-SITU MDF VELOCITY OF DETONATION

(75) Inventors: Frank M. Horine, Albuquerque, NM (US); Forrest B. James, Jr., Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1 day.

(21) Appl. No.: 10/714,703

(22) Filed: Nov. 17, 2003

(51) Int. Cl.[7] .............................................. G01N 33/22
(52) U.S. Cl. ..................................................... 73/35.15
(58) Field of Search .............................. 73/35.15, 167; 102/275.9

(56) References Cited

U.S. PATENT DOCUMENTS 3,670,559 A * 6/1972 Bement ..................... 73/35.15
4,379,401 A * 4/1983 San Miguel ................ 73/35.15
5,147,975 A   9/1992 Munach et al.
6,561,101 B1   5/2003 Smith

* cited by examiner

*Primary Examiner*—John E. Chapman
(74) *Attorney, Agent, or Firm*—Elmer A. Klavetter

(57) ABSTRACT

A system for determining the velocity of detonation of a mild detonation fuse mounted on the surface of a device includes placing the device in a predetermined position with respect to an apparatus that carries a couple of sensors that sense the passage of a detonation wave at first and second spaced locations along the fuse. The sensors operate a timer and the time and distance between the locations is used to determine the velocity of detonation. The sensors are preferably electrical contacts that are held spaced from but close to the fuse such that expansion of the fuse caused by detonation causes the fuse to touch the contact, causing an electrical signal to actuate the timer.

14 Claims, 2 Drawing Sheets

MEASURING IN-SITU MDF VELOCITY OF DETONATION

The United States Government has rights in this invention pursuant to Department of Energy Contract No. DE-AC04-94AL85000 with Sandia Corporation.

CROSS REFERENCE TO RELATED APPLICATIONS (Not Applicable)

BACKGROUND OF THE INVENTION

Mild detonating fuze (MDF) is a metal clad linear explosive usually drawn or extruded in a round configuration. Grain sizes can vary from 2.5 gr/ft to 100 gr/ft, and the metal sheath can be aluminum, tin, lead or silver. The diameter of MDF ranges from 40 mils or smaller to 250 mils or larger.

D. Smith, U.S. Pat. No. 6,561,101, shows a typical application where a length of MDF is used to delay a detonation after an input. The MDF is placed in a groove spiraling around the exterior surface of a metal case of a device. An electrically controlled igniter ignites one end of the MDF and the other end ignites an actuator. The length of MDF is chosen to provide a predetermined delay between ignition and actuation, the delay being a function of the length of MDF and the velocity at which the MDF detonates.

One problem that arises is that the velocity of detonation (VOD) for MDF may change over time. Such a change would change the actuation delay for devices such as ordinance that typically have a long shelf life between date of manufacture and date of use. For a quality check, VOD can be measured in a laboratory after the MDF is removed from a few stored devices. The average VOD for these devices is imputed to the remaining stored devices. However, handling the MDF introduces another variable that is not present in the stored devices, so the accuracy of this test is not certain.

SUMMARY OF THE INVENTION

It is an object of this invention to provide a system for measuring VOD directly from the stored devices without handling the MDF in those devices.

To achieve the foregoing and other objects, and in accordance with the purpose of the present invention, as embodied and broadly described herein, is a method of determining velocity of detonation of a metal-clad detonation fuze that expands in diameter as it detonates along its length, comprising the steps of placing a sensor spaced from and adjacent a first location on the fuze and placing a second sensor spaced from and adjacent a second location on the fuze. The fuze is ignited at a third location and it detonates along its length past the first and second locations. The expanded fuze is detected by each sensor as the fuze detonates at that sensor's location; and the velocity of detonation is determined from the time difference between the actuation of each sensor.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 1:
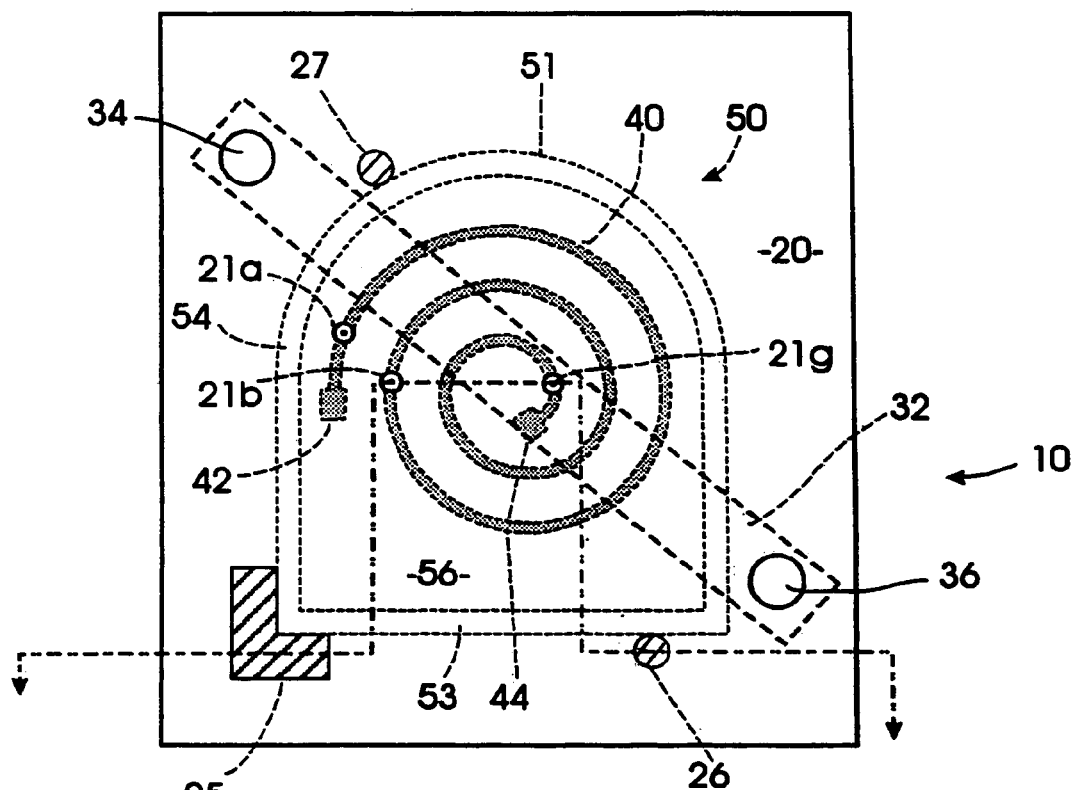
FIGS. 1 and 2 show top and cutaway side views, respectively, of the test fixture holding a device prior to measurement of VOD.
Figure 2:
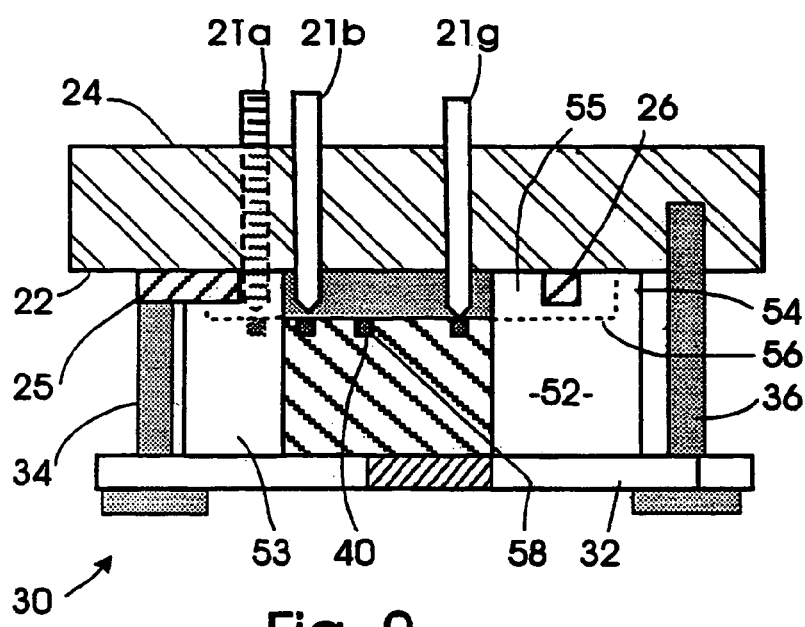

As shown in FIGS. 1 and 2, a test apparatus 10 and a device 50 to be tested are held together as discussed hereinafter. The test apparatus 10 includes at least two sensors 21a, 21b that are held at different positions slightly above an MDF 40 on device 50. MDF 40 expands when ignited and sequentially actuates each sensor. The time between actuation of the first and second sensors, coupled with the distance between the sensors, provides a measurement of VOD in MDF 40.

Apparatus 10 includes a body 20 that is preferably constructed from a rigid electrically insulating material. Body 20 is illustrated as being sized somewhat larger than the exterior dimensions of device 50 and has an interior surface 22 facing and interacting with device 50 and an opposed exterior surface 24. Apparatus 10 may also include a clamp 30 for holding device 50 tightly in a predetermined position against interior surface 22.

The particular device 50 illustrated includes a body formed as a metal block 52 having a generally rectangular shape rounded at one end 51 and squared at opposite end 53. Block 52 has a uniform thickness around its perimeter 54 and a thinner inner portion 56. This construction creates an open volume 55 between block portion 56 and body surface 22 when device 50 is clamped in position to body 20.

As further illustrated, a length of MDF 40 extends from an input igniter 42 at one end to an output igniter 44 at the opposite end within a groove 58 (shown in FIG. 3) formed in the surface of inner portion 56 that faces open volume 55. These igniters are conventional in the art (typical igniters are discussed in the Smith '101 patent) and may be embedded in holes inside device 50, on the surface 56 of device 50, or in any other location. The input igniter may be electrically actuated by a squib or similar device, while the output igniter typically is operationally connected to another explosive device. The output igniter and subsequent explosive device are not part of this invention.

Figure 3:
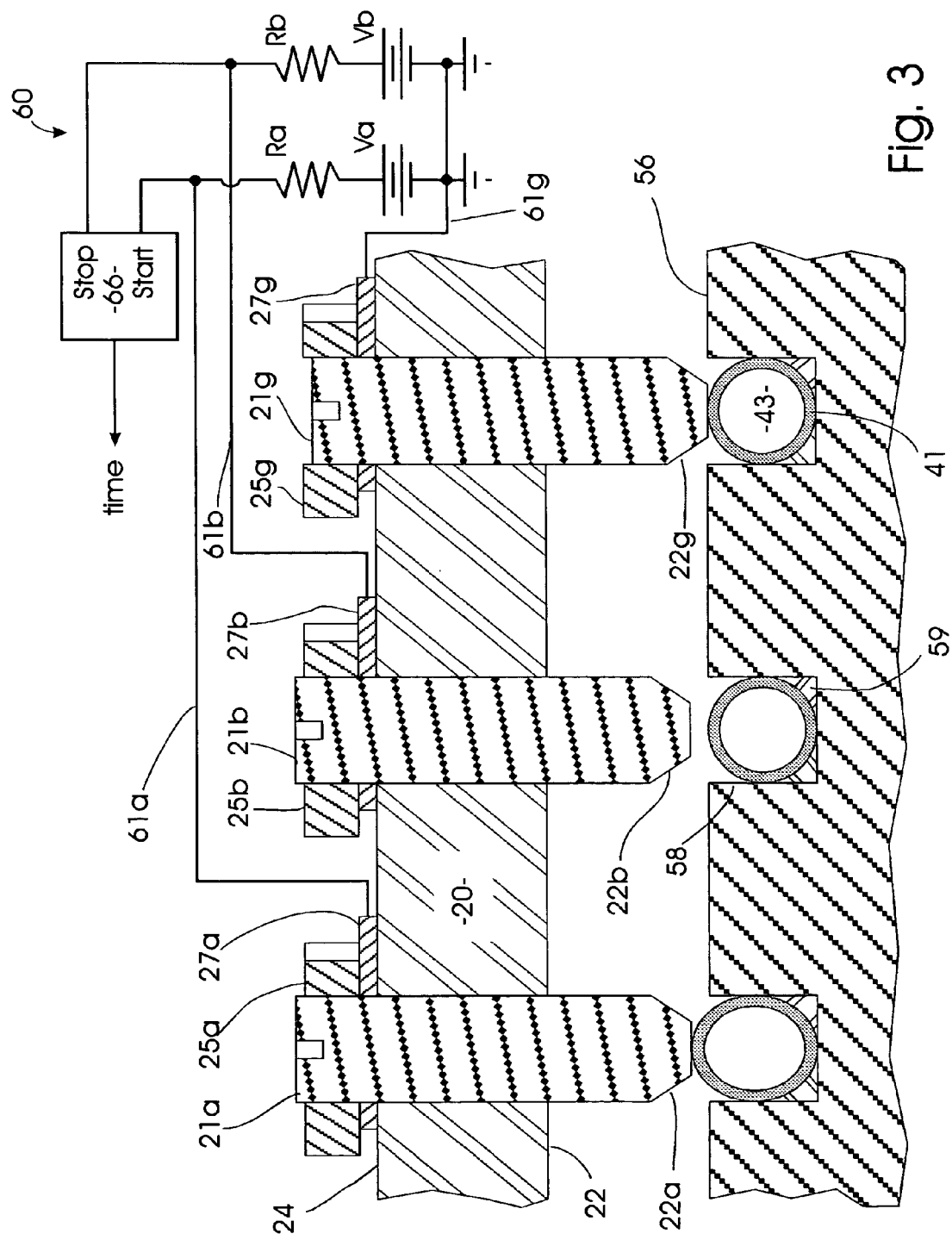
FIG. 3 is an enlargement of a portion of FIG. 2 during a measurement of VOD.

FIGS. 2 and 3 illustrate the relationship among MDF 40, groove 58, and conductors 21a, b, and g. In order to provide for in situ measurement of the VOD, apparatus 10 further comprises at least two spaced conductors 21a, b, for making contact with MDF 40 only after that MDF is ignited at end 42. MDF 40 is seen in cross-section in the referenced Smith '101 patent and FIG. 3 to have a thin aluminum or other metal cladding 41 surrounding an explosive 43. As illustrated under conductor 21b in FIG. 3, MDF 40 may be embedded in a room temperature vulcanizing adhesive 59 to hold it in place in groove 58. As illustrated in FIG. 2, a first conductor 21a is spaced above MDF 40 at a location near ignition end 42 and a second conductor 21b is similarly spaced above MDF 40 at a second location that is further along MDF 40 from ignition end 42 than the location of first conductor 21. The spacing is such that each conductor 21a, b does not make contact with cladding 41.

As illustrated in FIG. 3 with reference to conductor 21a, MDF 40 expands as the MDF explosive burns. Since the spacing between each conductor 21a, 21b and MDF 40 is less than the distance that an ignited MDF expands, the expanded MDF makes electrical contact with conductor 21a. A third conductor 21g can be placed in contact with ground, preferably by touching MDF 40 at a third location further along MDF 40 than the location of second conductor 22.

In the disclosed embodiment, each conductor 21 is a conventional 4-40 metal screw extending through a threaded hole in body 20 and having a tapered end 22. Each conductor further includes a tension nut 25 tightened against surface 24 through a conductive loop terminal lug 27 to put the screw under tension, so that it's depth may be accurately controlled. A wire 61 extends from each lug 27 to control circuitry 60. This structure permits screws 21a, b to be tightened against MDF 40 to ensure that a circuit is closed, and then backed off ¼ turn to provide for a 0.006 inch gap between MDF 40 and screw ends 22a,b. This gap is shown with respect to screw 21b.

Alternatively, as is apparent to those skilled in the art, the conductors could be pins or any other elongated structure that tightly and adjustably fit through an insulating sleeve in a metal block. In addition, the pin or screw could be an electrically insulating material with only an electrically conductive portion at the end for contacting MDF 40.

Device 50 must be precisely placed with respect to apparatus 10 in order for conductors 21 to contact MDF 40 at the desired locations. This precision can be attained by providing registering projections from interior surface 22 that interact with the edge of device 50 at different locations that limit the position of device 50 relative to interior surface 22 to the desired position. In the disclosed embodiment, projection 25 is an L-shaped member that positions one corner of device 50, while projections 26 and 27 are pins that hold opposing sides while still permitting device 50 to be slid into the proper position. These projections are disclosed as metal projections from a plastic block 20; but they also could be plastic. One of ordinary skill will recognize that many other registering techniques also can be used, such as pins on either block 20 or device 50 that fit into holes on the opposing structure, or indentations formed in the interior surface 22 that conform to the outline of block 50.

As disclosed, once device 50 is properly positioned against interior surface 22, it is held in place by a clamp 30 that is formed by a rigid bar 32 that spans the back side 58 of block 50 and which is held by screws 34, 36 that are tightened into interior surface 22. One of ordinary skill will recognize that many other holding techniques could be used, ranging from screws that extend through holes in device 50 into the interior surface 22 to other mechanical clamps that hold device 50 tightly against block 20.

In the preferred embodiment of the invention, circuitry 60 is a Digital Igniter Tester from Valhalla Scientific Co., San Diego, Calif. This device accurately measures the resistance as pins 21a and 21b contact MDF 40). However, for purposes of understanding the invention, the disclosed circuitry provides the desired function.

The basic idea is that an electrical circuit is sequentially completed at each conductor 21a, 21b when the detonation wave moves along and expands MDF 40 to contact the conductor, as shown at 21a in FIG. 3. Conductor 21g is grounded against MDF 40 and its wire 61g provides the ground for circuitry 60. A series battery Va and resistor Ra are connected to wire 61a and the 'start' input of digital timer 66. A similar battery Vb and resistor Rb are connected to wire 61b and the 'stop' input of timer 66. When either conductor is spaced from the MDF, as illustrated by end 22b in FIG. 3, no current flows through R and the voltage at timer 66 is V volts. However, when a conductor touches the MDF, as illustrated by end 22a in FIG. 3, the voltage at timer 66 is 0 volts.

To make a measurement in accordance with the invention, device 50 is clamped into apparatus 10 and screw end 21g is tightened against MDF 40. Each one of screw ends 21a or 21b is similarly tightened against MDF 40 and, after a closed circuit is observed using circuitry 60, the screw is backed off about ¼ turn to provide the desired gap. MDF 40 is then ignited and the time for the detonation wave to pass from screw 21a to screw 21b is determined by timer 66, which timer is turned on when the wave causes MDF 40 to contact screw end 22a and turned off when the wave causes MDF 40 to contact screw end 22b. Since the distance between these screws may be accurately measured, the VOD of detonation is easily calculated.

In one measurement made with the disclosed embodiment of the invention, the time for a detonation wave to move from conductor 21a to conductor 21b along 40 mil diameter MDF was 7.18 µs. Since the distance along MDF 40 was accurately determined to be 53.54 mm, the VOD is calculated to be 7.46 mm/µs.

The accurate measurement of the distance can be determined by replacing the MDF 40 with a drawn-hardened, identical diameter copper wire in device 50. This copper wire segment is marked by lowering pins 21a and 21b to slightly indent the copper wire column. The copper wire column is removed from the device 50 and straightened. The distance between the indent marks on the copper wire is measured using a calibrated optical comparator.

It should be apparent that there are many modifications possible with this invention, as long as the concept of using the expansion of MDF to actuate a sensor at multiple places along the MDF is followed.

Other sensors are also contemplated for use with this invention, such as self-contained switches being closed or capacitive sensors being actuated by the expanding MDF. In addition, different versions of the apparatus may be configured to work with any device shape.

If the device has a round configuration similar to that of the Smith '101 patent with MDF on the outside of a cylinder, the test apparatus can also have a similar configuration with spaced conductors extending from a concave body that fits over a portion of the cylindrical device. As before, the body holds spaced conductors over spaced locations along the MDF.

Furthermore, while it simplifies timing calculations for the sensors to be actuated sequentially as disclosed above, as long as the distance between the ignition point and each sensor is known, the ignition point could also be between the sensors along the MDF.

It is intended that the scope of the invention be defined by the appended claims.

What is claimed is:
1. A method of determining velocity of detonation of a metal-clad explosive fuze that expands in diameter as it detonates along its length, comprising:
  placing a sensor spaced from and adjacent a first location on the fuze;
  placing a second sensor spaced from and adjacent a second location on the fuze;

igniting the fuze at a third location on the fuze, wherein the fuze detonates along its length past the first and second locations, the expanded fuze being detected by each sensor as the fuze detonates at that sensor's location; and determining the velocity of detonation from the time difference between the actuation of each sensor;

wherein the sensors are mounted on an apparatus and the fuze is in a groove on a device, wherein the placing steps comprise:

holding the apparatus against the device in a fixed position with the first and second sensors vertically aligned with the respective first and second locations;

moving each sensor toward the fuze until it contacts the fuze; and moving each sensor to a sensing position that does not contact the fuze before detonation, and that will be contacted by the detonated fuze.

2. The method of claim 1 wherein the third location is not between the first and second locations.

3. The method of claim 2 wherein the ignited fuze actuates the first sensor before it actuates the second sensor.

4. The method of claim 3 wherein each sensor comprises an electrical conductor that contacts the fuze only after the fuze expands from detonation at the sensor.

5. The method of claim 4 further comprising an electrical circuit connected to each conductor, wherein actuation of each sensor causes a voltage change in the electrical circuit connected to that sensor.

6. The method of claim 1 wherein each sensor is a screw that extends through a block that covers the first and second locations, and the sensors are moved by screwing them towards and away from the fuze.

7. An apparatus for measuring the velocity of detonation in a mild detonation fuze extending in a groove on the surface of a device, the device including an igniter at one end of the fuze, said apparatus comprising:

a first sensor spaced from and adjacent a first location on the fuze;

a second sensor spaced from and adjacent a second location on the fuze, the second location being further along the fuze from the ignition end than the first location, said first and second sensors being spaced sufficiently close to the fuze that detonation at a sensor location is detected by the respective sensor;

registration structures operatively arranged to precisely position said first and second sensors with respect to the first and second locations, respectively; and a timer that is started when said first sensor detects an expanded fuze and is stopped when said second sensor detects an expanded fuze; wherein the velocity of detonation is calculated from time measured by said timer and the known distance between said first and second sensors.

8. The apparatus of claim 7, wherein said first and second sensors are electrical conductors that contact the fuze only after the fuze expands from detonation at the sensor.

9. The apparatus of claim 8, wherein said first and second sensors are screws retrievably extendible and electrically conducting and having tips pointing towards the first and second locations, respectively.

10. A method of determining velocity of detonation of a metal-clad explosive fuze, which expands in diameter as it detonates along its length, the method comprising:

placing a first sensor on a first module, wherein the first sensor is spaced from and adjacent a first location on the fuze, and wherein the fuze is placed on a second module;

placing a second sensor on the first module, wherein the second sensor is spaced from and adjacent a second location on the fuze;

positioning precisely the first and second sensors with respect to the first and second locations, respectively, using registration structures on the first module;

igniting the fuze at a third location on the fuze, wherein the fuze detonates along its length past the first and second locations, the expanded fuze being detected by the first and second sensors as the fuze detonates at that sensor's location; and determining the velocity of detonation from the time difference between the actuation of the first and second sensors.

11. The method of claim 10 wherein the third location is not between the first and second locations.

12. The method of claim 10 wherein the ignited fuze actuates the first sensor before it actuates the second sensor.

13. The method of claim 10 wherein the first and second sensors are electrical conductors that contact the fuze only after the fuze expands from detonation at the sensor.

14. The method of claim 10 wherein the first and second sensors are screws retrievably extendible and electrically conducting and having tips pointing towards the first and second locations, respectively.

* * * * *